United States Patent [19]
Wood

[11] 3,965,196
[45] June 22, 1976

[54] HYDROCARBON RECOVERY PROCESS

[75] Inventor: William Laurence Wood, Farnham, England

[73] Assignee: Davy Powergas Limited, England

[22] Filed: Mar. 7, 1975

[21] Appl. No.: 556,272

Related U.S. Application Data

[63] Continuation-in-part of Ser. No. 235,305, March 16, 1972, Pat. No. 3,914,277.

[52] U.S. Cl. ............................................. 260/604 R
[51] Int. Cl.² ......................................... C07C 45/04
[58] Field of Search ............................... 260/604 R

[56] References Cited
UNITED STATES PATENTS
3,312,719  4/1967  Hullstrung et al. ............. 260/604 R OTHER PUBLICATIONS
Kirkbride et al, Chem. Abst., vol. 38, 853⁹, 1944.

Primary Examiner—James O. Thomas, Jr.
Assistant Examiner—W. B. Lone
Attorney, Agent, or Firm—Morton, Bernard, Brown, Roberts & Sutherland

[57] ABSTRACT

In a process for preparing methacrolein by oxidation of isobutane, unreacted isobutane is absorbed from a gaseous mixture by absorption in a liquid absorbent and recovered by stripping the absorbent with nitrogen or a mixture of nitrogen and oxygen. The recovered isobutane in admixture with the stripping gas is then recycled to the oxidation reaction.

16 Claims, 1 Drawing Figure

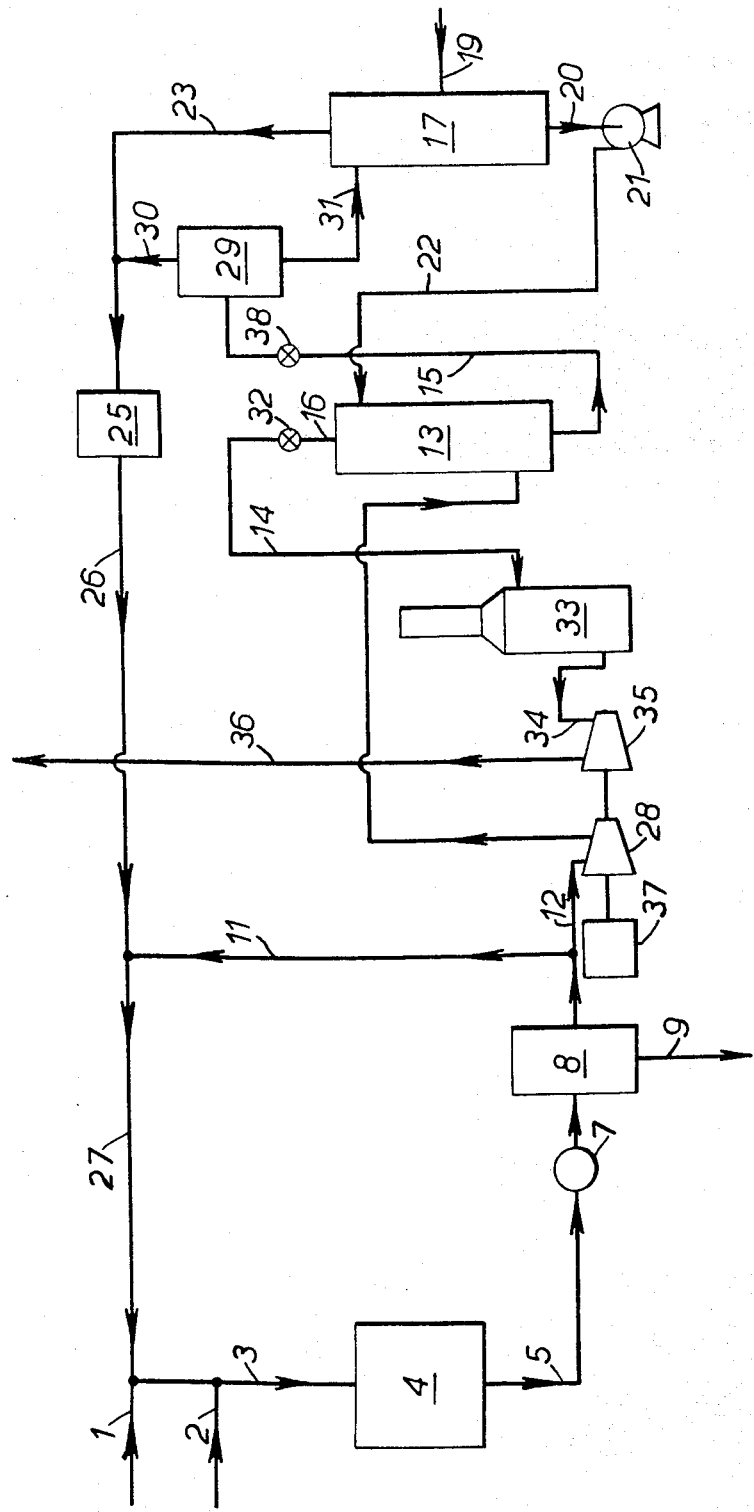

HYDROCARBON RECOVERY PROCESS

This application is a continuation-in-part application of U.S. patent application Ser. No. 235305 filed on Mar. 16, 1972, U.S. Pat. No. 3,914,277 and the invention relates to processes for recovering isobutane from mixtures of gases.

In some oxidation reactions in which an alkane is involved, such as that described in British (patent) specification No. 1340891, it is found that an improved reaction efficiency can be obtained by operating with a high concentration of the alkane and a low concentration of oxygen. This leads to the conversion in the reactor of only a small proportion of the hydrocarbon supplied to the reactor and gives a product gas which will have a hydrocarbon content several times that of the desired product. After removal of the desired product all of the unconverted hydrocarbon could be recycled to extinction, except that it is usually contaminated with by-products formed during the reaction, such as carbon dioxide, and/or by unreactive material introduced with the feedstock, such as nitrogen.

It is necessary to remove these contaminants from the cycle at the rate at which they are produced or introduced to prevent their concentration building up and displacing the reactants and thus stopping the reaction. The contaminants, which contain permanent gases, are difficult to remove from the hydrocarbon by any economic means and it is preferable to recover the hydrocarbon from the gas stream after removing the desired product and to return the recovered hydrocarbon to the reactor. It is possible but not necessary to treat the whole of the product stream in this manner, it being preferred to carry out hydrocarbon recovery on a purge stream only.

The contaminant concentration in the purge stream will depend on the purge rate, among other things. This rate is determined from an economic balance between the marginal cost of equipment and utilities incurred in recycling contaminants around the system and the cost of recovery of hydrocarbon from the purge stream, such latter cost depending on the purge gas volume.

An object of the present invention is to provide an improved method of recovering the isobutane from the purge stream in a process for the preparation of methacrolein by oxidation of isobutane.

It is known that light hydrocarbons, i.e. principally $C_2$ to $C_5$ hydrocarbons, can be removed from a stream of which the other constituents are permanent gases, e.g. natural gas, i.e. methane, by absorbing the light hydrocarbons in an absorption column in which the gaseous mixture passes in counter-current flow to a wash oil. The oil has a vapour pressure relatively low compared with the hydrocarbons to be removed, but has a highly selective power of absorption for the latter compared with the permanent gases.

The conventional method of recovering these light hydrocarbons from the wash oil has been to pass the enriched oil down a heated stripping column, using steam or wash oil vapour as the stripping medium. This involves heating the oil to a temperature above which steam will not condense or to a temperature at which the wash oil will boil, whichever is the lower, at the pressure at which the stripping column is operated.

We have now found that means for the provision of this heat, and its cost, may be avoided by using nitrogen or a mixture of nitrogen and oxygen as a stripping medium, preferably in an adiabatic system, and passing such stripping gas, in admixture with the recovered isobutane, to the reactor feed stream.

Thus, according to the invention there is provided in a process for the preparation of methacrolein by oxidation of isobutane in which the effluent from the oxidation contains unreacted isobutane, carbon oxides, nitrogen, and methacrolein, in which said methacrolein is removed from the oxidation effluent, and in which unreacted isobutane is separated from carbon oxides and nitrogen in the oxidation effluent and recycled to the oxidation reaction, the improvement which comprises contacting said oxidation effluent from which said methacrolein has been removed with a liquid absorbent to absorb said unreacted isobutane and none or only a minor portion of said carbon oxides and nitrogen, contacting resulting liquid absorbent containing isobutane with nitrogen or a mixture of oxygen and nitrogen as a stripping gas to strip isobutane from said liquid absorbent and obtain a gaseous effluent containing isobutane and stripping gas, and passing said gaseous effluent to said oxidation reaction.

When a mixture of nitrogen and oxygen is used for stripping it preferably contains at least 30% and more preferably at least 50% nitrogen by volume. It is most convenient to use air for the stripping.

The isobutane feedstock for the oxidation reaction produces the corresponding unsaturated aldehyde product. The partial pressure of the isobutane in the oxidation reaction is preferably at least 0.20 atmospheres absolute, more preferably at least 0.35 and most preferably at least 0.70 atmospheres absolute. The reaction is preferably carried out at a feed gas pressure of 1 to 5 atmospheres absolute. The temperature desirably does not exceed 500°C for the efficiency of the oxidation reaction, but the present process can of course be employed regardless of what the reaction temperature may be.

Any liquid may be used as the liquid absorbent, provided that it absorbs the feedstock isobutane, whilst absorbing substantially none or only a minor proportion of the gases from which the hydrocarbon is to be separated, and that it can be stripped of the isobutane by the said nitrogen or mixture of nitrogen and oxygen. Suitable liquid absorbents are, inter alia, light oils, paraffinic in nature, having 10 to 17 carbon atoms, e.g. kerosene, heavy naphtha or light gas oil. Hydrocarbon oils, lighter than $C_{10}$ can be used, particularly at low temperatures, but tend to vaporise too easily at normal temperatures. Very heavy oils tend to be too viscous and give low tray efficiencies in columns in which the stripping and absorption are preferably carried out. Among other suitable liquids are acetone and isopropyl alcohol although it is necessary in the case of these absorbents to water wash them out of overhead gases from the absorption and stripping columns if absorbent is not to be lost and if absorbent is not to be fed to the reactor with the recovered isobutane.

It will usually be found preferable to operate the stripping column at a pressure exceeding the pressure in the reactor by only a small amount, e.g. by 0.10 to 20 psi and preferably less than 5 psi. The pressure chosen for the absorption column depends on the efficiency of the conversion reaction, the volume of gas used in the stripping column and its nitrogen content, and the concentration of the feedstock isobutane in the reactor.

When air is used as the stripping gas, it will be found necessary to compress the stream from which isobutane is to be recovered so as to operate the absorption column at a pressure substantially higher (typically 3 to 4 times higher) than that of the stripping column. The ratio of absorption column/stripping column pressure varies with each reaction and with any alteration in reaction conditions. In general it is in the range 2:1 to 7:1 and preferably 2.5:1 to 4:1.

The invention will be more readily understood from the following example of a method of recovering isobutane from a mixture of gases resulting from an oxidation reaction, reference being made to the accompanying drawing, FIG. 1, which shows a process in which the isobutane is absorbed in kerosene and air is used for stripping the absorbed isobutane.

The isobutane oxidation is operated, as a recycle process, with a feed gas of isobutane and air at low conversions of isobutane per pass through a reactor (referred to below), but relatively high conversions of oxygen. By "conversion" is meant the difference in the amounts of the substance in question in the feed gas and exit gas divided by the amount of the substance in the feed gas. Typically the process is operated at 400° to 500°C and at 2 to 4 atmospheres absolute with an isobutane partial pressure of 0.7 to 1.6 atm. Conversions of isobutane and oxygen are, for example, 10% and 90% respectively.

Isobutane make-up and air are fed through lines 1 and 2 respectively, meeting a recycled air/isobutane mixture in line 27, to pass into a reactor 4 in this case at 55 psia. Exit gases from the reactor pass by line 5 to a recycle compressor 7 and pass to an aldehyde recovery system 8. The unconverted isobutane leaves this system, accompanied by oxides of carbon and nitrogen. Because air is used, the nitrogen will represent a substantial proportion (approximately 50%) of the stream. If the conversion of isobutane is less than 10%, the stream is split into two portions, one in line 11 and the other in line 12, that in line 12 representing the purge stream passing to the isobutane recovery system and that in line 11 by-passing this system. With a conversion of isobutane of 3% the volumetric ratio of gas passing through the line 11 to that in the line 12 is 2.4:1.

The gaseous mixture in line 12 is fed to a compressor 28 to raise the pressure of the mixture to 160 to 180 psia before being passed to an absorption column 13. This pressure is high enough to ensure substantially complete removal of the isobutane in the absorption column 13 from the associated oxides of carbon and nitrogen when using the maximum flow of kerosene which can be stripped of isobutane by the air.

At sufficiently high conversions of isobutane, i.e. in general at least 10% conversion, it is preferable not to split the gas stream from the recovery systems, but to feed the entire stream to the column 13 (i.e. the line 11 is eliminated). In this latter case the compressors 7 and 28 are replaced by a single machine.

The pressure in the absorption column 13 is high enough to dispense with a pump for transferring the isobutanerich absorption liquid to the top of a stripping column 17 and it simply flows by line 15, via a pressure reduction valve 38, to a liquid/gas separator 29 from the head of which any gaseous isobutane which has been liberated from the absorption liquid by pressure reduction leaves by line 30, leaving the remaining dissolved isobutane to pass by line 31 to the top of the stripping column 17. Alternatively, the column 17 and the separator 29 can be combined in a single tower.

The stripping column is operated at a pressure of 58 psia. The liquid passes down this column being met by an upward flow of air introduced through line 19 to the base of the column. It is normally found advantageous to use all of the air required for stripping in this column to minimise the pressure required in the absorption column. The flow rate of the kerosene in the absorption and stripping columns and the above mentioned pressure in the absorption column are chosen so that the columns can be designed with a reasonable number of trays. The flow rate of purge gas to the absorption column is 4619 kg. mols per hour, the gas containing 40.3% isobutane. The lean kerosene flow rate is 4070 kg. mols per hour. Lastly, the flow rate of air to the stripping column is 3173 kg. mols per hour.

The kerosene, stripped of its isobutane, is passed back to the head of the absorption column 13 by line 20, pump 21 and line 22 whilst the recovered isobutane passes by line 23 from the head of the stripping column in admixture with the air supplied at the base of the column. This mixture then meets the isobutane from line 30, which had been liberated from the isobutane-rich kerosene on pressure reduction and passes to a vapour removal unit 25 for removal of kerosene vapour by lowering the temperature with resultant condensation or absorption on a solid. From the unit 25 it leaves by line 26 to meet the by-pass stream in line 11 and passes by line 27 back to the reactor 4.

The gas which leaves the top of the absorption column 13 by line 14 and from which the isobutane has been almost completely removed, passes through a back-pressure control valve 32 and then through a heater or tail gas oxidation unit 33 before entering an expansion turbine 35, via line 34. The turbine 35 is coupled to the shaft of the compressor 28. The purge gases finally pass to waste at atmospheric pressure through line 36. It is found that a substantial portion of the power required by the compressor 28 can be provided by the expansion turbine 35 and the remainder can be provided by any suitable prime mover 37, also coupled to the compressor shaft.

It is claimed:

1. In a process for the preparation of methacrolein by oxidation of isobutane in which the effluent from the oxidation contains unreacted isobutane, carbon oxides, nitrogen, and methacrolein, in which methacrolein is removed from the oxidation effluent, and in which unreacted isobutane is separated from carbon oxides and nitrogen in the oxidation effluent and recycled to the oxidation reaction, the improvement which comprises contacting said oxidation effluent from which methacrolein has been removed with a liquid absorbent to absorb said unreacted isobutane and none or only a minor portion of said carbon oxides and nitrogen, contacting resulting liquid absorbent containing isobutane with nitrogen or a mixture of oxygen and nitrogen as a stripping gas to strip isobutane from said liquid absorbent and obtain a gaseous effluent containing isobutane and stripping gas, and passing said gaseous effluent to said oxidation reaction.

2. A process according to claim 1 in which the stripping gas is a mixture of nitrogen and oxygen containing at least 30% nitrogen by volume.

3. A process according to claim 2 in which the stripping gas is a mixture of nitrogen and oxygen containing at least 50% nitrogen by volume.

4. A process according to claim 3 in which the stripping gas is air.

5. A process according to claim 1 in which the absorbent liquid is a paraffinic oil containing 10 to 17 carbon atoms.

6. A process according to claim 5 in which the absorbent liquid is an oil selected from the group kerosene, heavy naphtha, and light gas oil.

7. A process according to claim 1 in which all of the gas from which desired product is removed is treated for said absorption and recovery of isobutane.

8. A process according to claim 1 in which only a portion of the gas from which desired product is removed is treated for said absorption and recovery of isobutane.

9. A process according to claim 1 in which the partial pressure of the isobutane in the oxidation reaction is at least 0.20 atmosphere absolute.

10. A process according to claim 9 in which the said partial pressure is at least 0.35 atmosphere absolute.

11. A process according to claim 10 in which the said partial pressure is at least 0.70 atmosphere absolute.

12. A process according to claim 9 in which the oxidation reaction is carried out at a pressure of from 1 to 5 atmospheres absolute.

13. A process according to claim 1 in which the stripping is carried out in a stripping column operated under a pressure of 0.10 to 20 psi above the pressure of the oxidation reaction.

14. A process according to claim 13 in which the stripping column is operated under a pressure of less than 5 psi above the pressure of the oxidation reaction.

15. A process according to claim 1 in which the absorption is carried out in an absorption column which is operated at a pressure which is 3 to 4 times higher than the pressure of the oxidation reaction.

16. A process according to claim 13 in which the ratio of absorption column pressure to stripping column pressure is 2.5:1 to 4:1.

* * * * *